United States Patent [19]
Igushi et al.

[11] Patent Number: 6,061,131
[45] Date of Patent: *May 9, 2000

[54] OPTICAL AXIS ADJUSTMENT APPARATUS AND METHOD FOR PARTICLE SIZE DISTRIBUTION MEASURING EQUIPMENT

[75] Inventors: Tatsuo Igushi; Yoshiaki Togawa, both of Miyanohigashi-machi, Japan

[73] Assignee: Horiba, Ltd., Kyoto, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/780,592

[22] Filed: Jan. 8, 1997

[51] Int. Cl.[7] ................................................. G01N 15/02
[52] U.S. Cl. ........................... 356/336; 356/343; 356/335
[58] Field of Search .................................. 356/335–343, 356/73, 399; 250/564, 574

[56] References Cited

U.S. PATENT DOCUMENTS 5,007,737   4/1991   Hirlman et al. ........................ 356/336
5,737,078   4/1998   Takarada et al. ....................... 356/336

FOREIGN PATENT DOCUMENTS 5273114   10/1993   Japan .

*Primary Examiner*—Robert H. Kim
*Attorney, Agent, or Firm*—Price Gess & Ubell

[57] ABSTRACT

A light scattering particle size distribution measuring apparatus inches a light source for providing a beam of light to contact with a sample cell holding a specimen. A detector assembly includes a first set of detector assembly includes a first set of detector elements for receiving scattered and/or diffracted light from the sample cell and a second set of detector elements positioned between the first set of detector elements. A removable scattering and/or diffracting target member can be positioned on the optical axis to provide a predetermined scattered and/or diffraction pattern to the detector assembly whereby the second set of detector elements can measure the predetermined fraction pattern to enable a movement of one of the light source and the detector assembly to align them on an optical axis.

8 Claims, 4 Drawing Sheets

OPTICAL AXIS ADJUSTMENT APPARATUS AND METHOD FOR PARTICLE SIZE DISTRIBUTION MEASURING EQUIPMENT

BACKGROUND OF THE INVENTION

1. Field of the Invention

The present invention relates to a method and apparatus for adjusting the alignment of components on an optical axis in a scattering type particle size distribution measuring equipment by irradiating a diffracting target member with light from a light source, directing the scattered light in such event into a photo-detector via a condenser lens, and measuring the scattered light intensity patterns projected at a specific predetermined location in the photo-detector.

2. Description of the Prior Art

The determination of particle sizes in a sample by their scattering of light is well known in the prior art. FIG. 4 shows a principal portion of a general scattering type particle size distribution measuring equipment, in which numeral 1 denotes a laser tube emitting laser beam 2, numeral 3 is a beam expander for expanding a laser beam 2 as required, numeral 4 is a sample cell for storing the sample 5, numeral 6 is a beam condenser lens mounted behind the cell 4, numeral 7 is a photo detector comprising photo diodes for detecting scattered light from the light condenser lens 6, numeral 8 is a multiplexer for taking in signals from the photo detector 7, and numeral 9 is a CPU to which signals are entered from the multiplexer 8 and which carries out computations based on the scattered light intensity patterns to determine the particle size distribution.

In the scattering type particle size distribution measuring equipment, storing the sample 5 in the cell 4 and irradiating the sample cell 4 with the laser beam 2 causes part of the laser beam 2 to irradiate particles in the sample 5 inside the cell 4 and to become scattered light 10, and the remainder of light passes between particles and becomes transmitted light 11. Both scattered light 10 and transmitted light 11 reach the photo detector 7 via the light condenser lens 6.

Now, in such a scattering type particle size distribution measuring equipment, the optical axis of the laser tube 1 of the light source must strictly coincide with that of the photo detector 7, but if the laser tube 1 is subject to thermal stress, or a bench (not illustrated) equipped with the cell 4, lens 6, photo detector 7, etc. is distorted by heat, or the cell 4 is exchanged, the optical axis location is sometimes changed and deviation occurs.

Therefore, in the conventional scattering type particle size distribution measuring equipment, on the center portion 7A of the optical axis of the photo detector 7, for example, a 4 part-split type light receiving portion 12 for adjusting the optical axis comprising photo diodes is mounted as shown in FIG. 5, and the position of the photo detector 7 is adjusted in such a manner to obtain an equal magnitude of the intensity signals outputted from the four light receiving elements, 12a–12d, respectively, which constitute the light receiving portion 12 for optical axis adjustment to, thereby adjusting the optical axis.

In FIG. 5, numeral 7 denotes a measuring portion for detecting scattered light comprising a plurality of scattered light receiving elements 13a, 13b, 13c, . . . 13n, which are concentrically mounted within the light receiving portion for optical axis adjustment 12 as a center and numeral 14 are isolation gaps provided between the scattered light receiving elements 13a–13n.

In order to carry out an optical axis adjustment as described above, the light receiving portion for optical axis adjustment 12 must be designed to have a radius equivalent to or greater than the size of the variation of a laser beam emitted from the laser tube 1, and if the laser beam varies, for example, by 100 μm at maximum, a 100-μm-in-radius light receiving portion for optical axis adjustment 12 is required for measuring the variation.

Now, in a scattering type particle size distribution equipment, because the greater the diameter of the particle, the smaller is the angle made with the optical axis of the scattered light, it is necessary to form a measuring portion for scattered light detection 13 at a position close to the optical axis center portion 7A, but if a significant size of the light receiving portion for optical axis adjustment 12 is provided as described above, it is unable to provide the scattered light receiving element 13a, etc., in the vicinity of the optical axis center portion 7A, and consequently, a certain limitation has been generated in measuring large-size particles.

Thus the prior art is still seeking an improvement in the operation of a light scattering particle distribution measuring equipment

SUMMARY OF THE INVENTION

In view of the foregoing, it is the main object of this invention to provide an apparatus and a method for adjusting the optical axis in a scattering type particle size distribution measuring equipment (hereinafter simply called the "optical axis adjustment methods") which can precisely adjust the optical axis even when scattered light receiving elements are mounted sufficiently close to the optical axis center portion of the photo detector.

In order to achieve the above-mentioned object, in this invention, on the optical axis connecting the light source to the photo detector, a means for generating a predetermined diffracted light or scattered light pattern is mounted, and using the diffracted light or scattered light generated by this means for generating diffracted light or scattered light, the optical axis is adjusted.

In this invention, light from a light source is irradiated over the sample, and the diffracted light or scattered light in such event is allowed to impinge on the photo detector via a condenser lens, and in the scattering type particle size distribution measuring equipment for measuring the particle size distribution in the sample based on the scattered light intensity pattern obtained in this event, a means for generating diffracted light or scattered light is mounted in the optical path from the light source to the condenser lens and at the same time three or more diffracted light or scattered light detectors are equally arranged around the optical axis center portion of the photo detector in such a manner to prevent overlapping of the detection portion for scattered light measurement forming the photo detector, and the optical axis is adjusted by changing the position of either the photo detector or the light source in such a manner that each output becomes equal when the diffracted light or scattered light generated when the light from the light source passes the means for generating diffracted light or scattered light impinges on the diffracted light or scattered light detector.

For the means for generating diffracted light or scattered light, for example, a pinhole may be formed on a sheet body which interrupts the light, or conversely, a small-diameter light-shielding portion may be formed in a light-transmittable sheet body. In either case, a desired diffracted light or scattered light pattern can be obtained with a diffracting or scattering target member.

The diffracting or scattering target member can be movably mounted at a predetermined location in the light scattering particle distribution measuring equipment in order to permit an operative positioning of the diffracting or scattering target member for calibration and the removal of the diffracting or scattering target member for a measurement mode of operation.

The photo detector is further modified to position, within the gaps between the light receiving elements, a second set of detectors of a size relative to the diffracting or scattering target member to receive the diffracted or scattered light from the target member. For example, diffracted light in accordance with Fraunhofer's equation can be provided by the target member and the second set of detectors can be positioned within the gap of the primary or first set of light receiving elements to enable a relative adjustment of components to an optical axis.

In carrying out the adjustment based on the light intensity by the diffracted light or scattered light, the accuracy of the optical axis position is able to be further improved if the optical axis is fine-adjusted to maximize the light condensed by the condenser lens.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an optical axis adjustment apparatus and method for particle size distribution measuring equipment.

Figure 4:
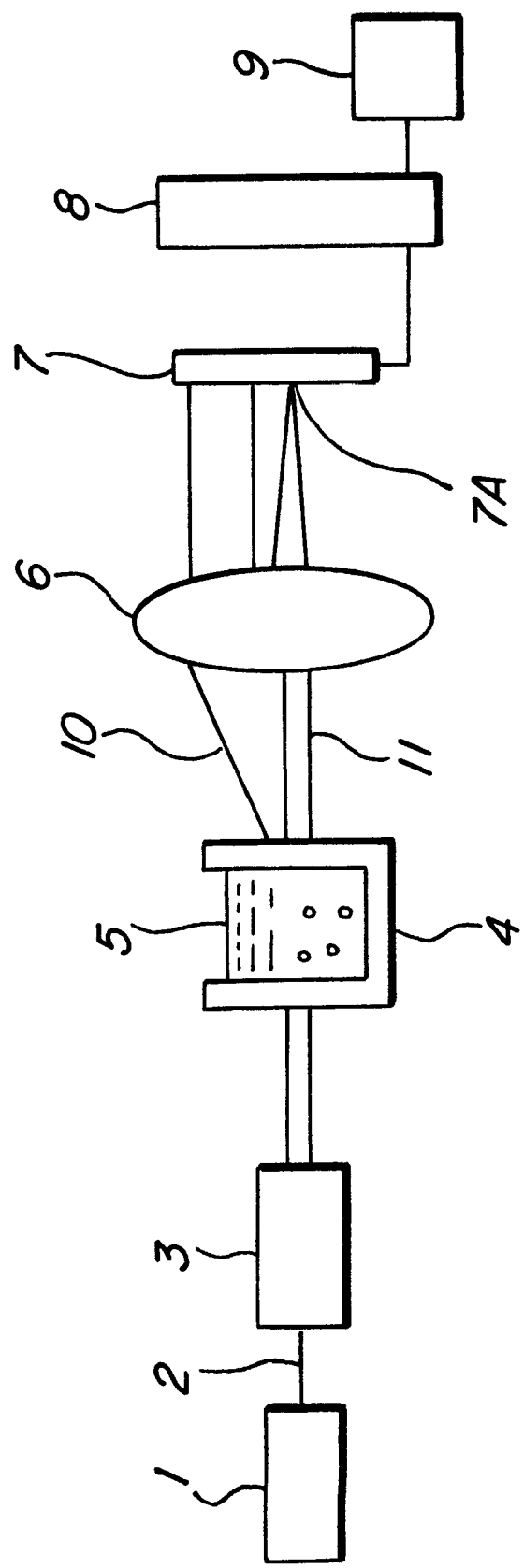
FIG. 4 is schematic representation showing the configuration of a general scattering type particle size distribution measuring equipment.
Figure 5:
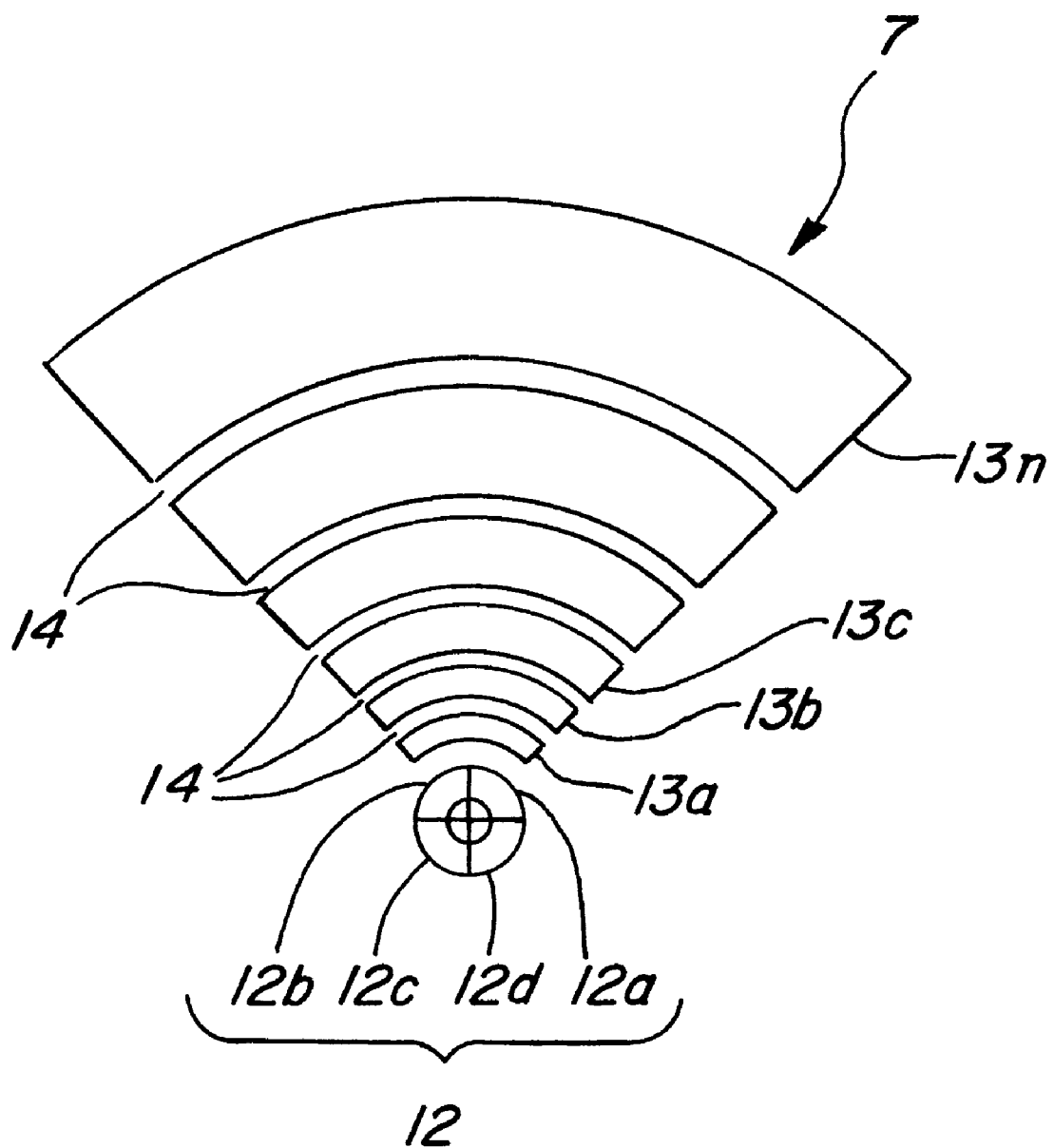
FIG. 5 is a schematic representation of a planar structure of the photo detector of the scattering type particle size distribution measuring equipment used in FIG. 4.

Referring now to the drawings, the embodiment of the present invention is described in detail as follows. In the following drawings, since components which are represented by the drawing symbols shown in FIG. 4 and FIG. 5 represent the same things, a further explanation of those elements will be omitted.

Figure 1:
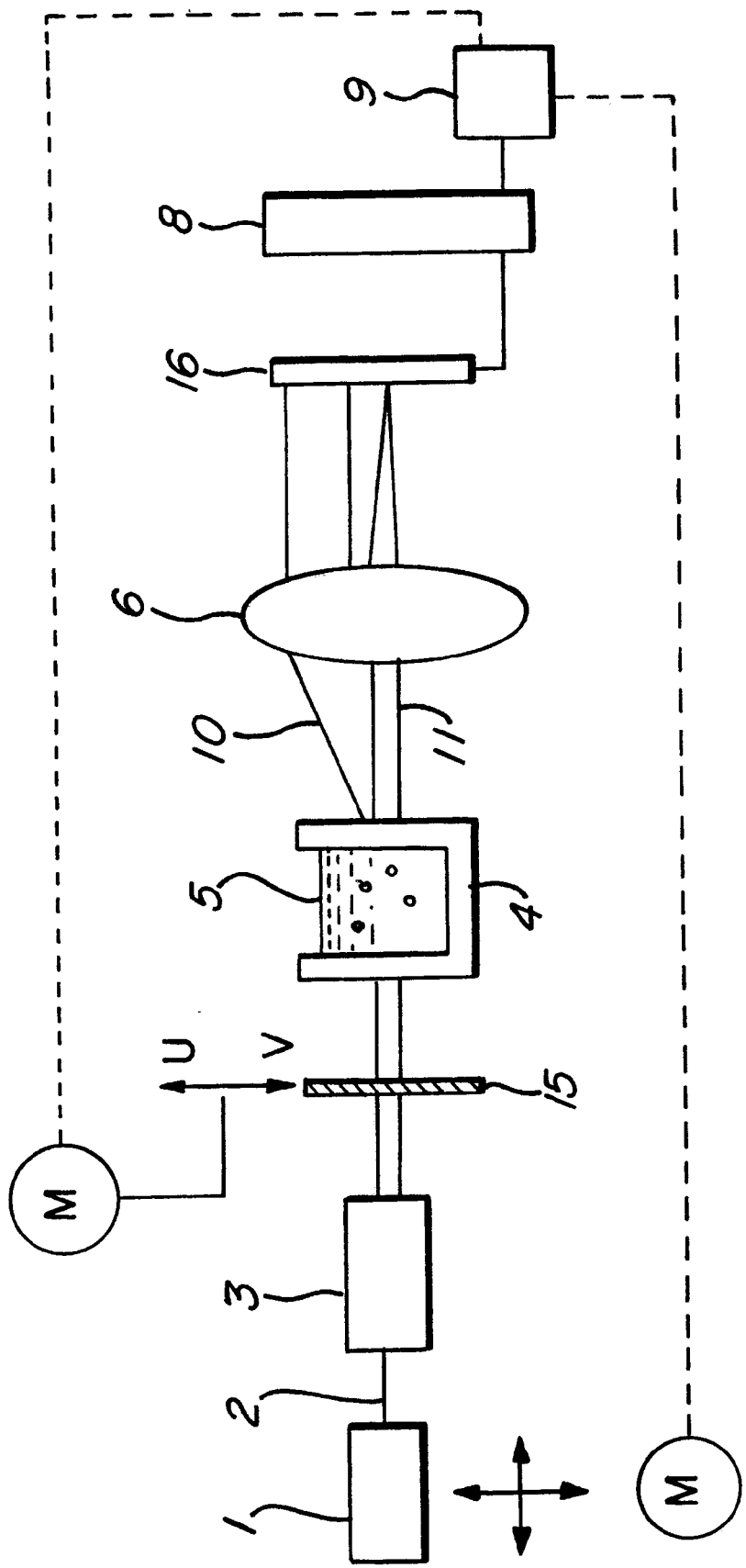
FIG. 1 is a schematic representation showing one example of the scattering type particle size distribution measuring equipment to which the optical axis adjustment method according to this invention is applied.
Figure 2:
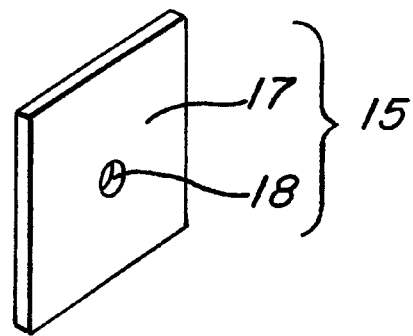
FIG. 2 is a perspective view showing one example of the means for generating diffracted light or scattered light used in the optical axis adjustment method.

FIG. 1 shows a configuration of a scattering type particle size distribution measuring equipment to which this invention is applied. This scattering type particle size distribution measuring equipment is basically the same as the scattering type particle size distribution measuring equipment shown in FIG. 4, but it greatly differs in that a means for generating diffracted light or scattered light 15, used in adjusting the optical axis, is removably mounted in the optical path from the laser tube 1 and the light condenser lens 6 and in that the diffracted light or scattered light generated by this means for generating diffracted light or scattered light 15 is particularly designed to provide a predetermined diffraction pattern to be detected by the photo detector 16. These will be described in further detail as follows FIG. 2 shows one example of the means for generating diffracted light or scattered light 15 and in this drawing, numeral 17 is a sheet material comprising light-shielding or opaque material, at the nearly center of which a pinhole 18 is apertured of a predetermined size.

The diffracting scattering target member 17 can be moved into and out of the line of sight of the laser tube 1 by conventional elements such as a motor, guide tracks, etc., and can be automatically controlled by a CPU 9 to start a calibration mode of operation. The location of the diffracting or scattering target member 17 is predetermined relative to the location of the photo detector 16 to enable a relative adjustment of the alignment of the laser tube 1 or the photo detector 16 during calibration. For example, the laser tube 1 could be moved to an on axis position relative to the photo detector 16, or the photo detector 16 could be moved. The dotted control lines in FIG. 1 disclose the automatic calibration mode that can be controlled by the CPU 9.

Figure 3:
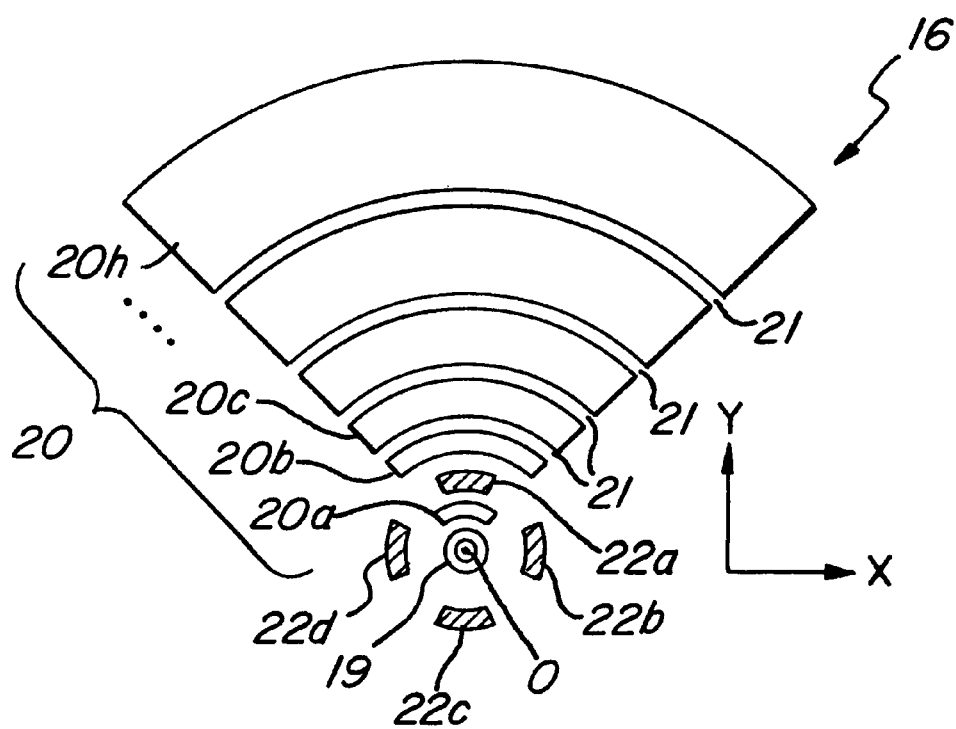
FIG. 3 is schematic representation showing the planar structure of the improved photo detector of the scattering type particle size distribution measuring equipment.

FIG. 3 shows one example of the planar structure of the improved photo detector 16 of the present invention and in this drawing, numeral 19 is a detector for monitoring outputs to be mounted at the optical axis center portion 0 of the photo detector 16 and is equipped with a light receiving portion equivalent in size to the beam diameter of the laser beam 2. Numeral 20 is a measuring portion for scattered light detection comprising a plurality of a first set of diffracted or scattered light receiving elements 20a–20n mounted in a fan shape and concentrically with a spreading angle of 90° with the optical axis center portion 0 (detector for monitoring output 19) as a center, and numeral 21 are isolation gaps provided between the scattered light receiving elements 20a–20n. Numerals 22a–22d are a second set of diffracted light (or scattered light) detectors mounted at a position centered around the detector 19 for monitoring a predetermined diffraction or scattering pattern output and at the same time not overlapping the first set of scattered light receiving elements 20a–20n, and in the illustrated example, they are mounted to be equally spaced about the circumference of the detector 19. By selecting a particular scattering diffraction output from the diffracting or scattering target member 19, the position and size of the second set of diffracted or scattered light detectors 22a–22d can be optimized within a predetermined gap position of the first set of detectors 20–20n without interfering with their normal operation during a measurement mode of operation.

In the scattering type particle size distribution measuring equipment of the above configuration, in the case of measuring the particle distribution of the sample 5, laser beam 2 is irradiated by the laser tube 1 with the sample 5 stored in the cell 4. In this event, a means for generating diffracted light or scattered light 15 moves in the arrow U direction in FIG. 1 and is evacuated from the optical axis to prevent obstruction to measurement. Particles in the sample 5 inside the cell 4 are irradiated with part of the laser beam 2 to become scattered light 10, and the remainder of the light passes between particles to become transmitted light 11. Both these scattered light 10 and transmitted light 11 reach the photo detector 16 via the condenser lens 6. The output of the photo detector 16 obtained in this event is inputted to CPU 9 via a multiplexer 8, and by carrying out known algorithm computations based on the diffracted or scattered light intensity pattern in the CPU 9, the particle size distribution can be determined.

In the case of a calibration adjustment of the optical axis, the means of generating diffracted light or scattered light 15 is moved in the arrow V direction and interposedly mounted between the beam expander 3 and the cell 4 at a predetermined position. When the laser beam 2 is emitted in the cell direction under this condition, diffracted light or scattered light approximated by the following Fraunhofer's diffraction I is generated.

$$I = I_0(J_1(x)/x)^2$$

$$x = 2\pi rs/\lambda f$$

where λf:wavelength
r:pinhole radius
s:detector position
$J_1$:primary Bessel function
$I_0$:incident light intensity In this event, the diameter of the pinhole 18 provided in the sheet material 17 is set as required so that the diffracted light or scattered light generated by the means for generating diffracted light or scattered light 15 impinges on each diffracted light or scattered light detector 22 in the photo detector 16. Then, the position of the photo detector 16 is precisely moved so that outputs from the four diffracted light or scattered light detectors 22 become equal. The final position where the outputs of each of the diffracted light or scattered light detectors 22 become equal to one another is determined and the photo detector 16 is fixed to that position. The CPU 9 can provide an output representative of a position where the detectors 22 receive equal amounts of light. For example, in order to allow a light intensity of ½ the maximum diffracted light or scattered light intensity to come to a 50 μm position, the pinhole diameter 18 should be 320 μm. The diffracted light or scattered light in that event expands to 820 μm in radius. Consequently, an adjustable variation in the optical axis of the laser beam 2 within this range can be achieved.

As understood from FIG. 3, the second set of light receiving elements 22a–22d constituting the diffracted light or scattered light detector 22 are mounted at positions where they do not overlap with the first set of scattered light receiving elements 20a–20n of the measuring portion for scattered light detection 20, and in addition, they are arranged under the condition in which the element (20a in this case) inside the measuring portion for scattered light detection 20 is brought extremely close to the optical axis center portion 0 of the photo detector 16. Consequently, because the first set of light receiving elements of the measuring portion for scattered light detection 20 can be arranged considerably closer to the optical axis center portion 0, the resultant measurement of particles with a large diameter which have been previously difficult to measure can be satisfactorily carried out.

It is to be understood that the invention is not intended to be limited to the above-mentioned embodiment and that various changes and modifications may be made in the invention without departing from the spirit and scope thereof. For example, as a means for generating diffracted light or scattered light 15, it is possible to use a translucent member to which a small-diameter light shielding portion is formed. That is, the sheet material 17 shown in FIG. 2 can be made to be translucent, and in place of the pinhole 18, a predetermined size of spherical particles consisting of light-shielding material may be formed at this portion.

The means of generating diffracted light or scattered light 15 may automatically be inserted into and evacuated from the optical path with a suitable mechanism such as a motor and rack and pinion gear assembly and the means for generating diffracted light or scattered light 15 may be located at any predetermined place in the optical path, if it is between the laser tube 1 and the condenser lens 6.

The optical axis adjustment method is suitable for a scattering type particle size distribution measuring equipment in which the cell 4 is unable to be removed because the means for generating diffracted light or scattered light 15 is designed to be inserted with the cell 4 mounted in the optical path, but in place of this method, the cell 4 may be removed from the optical path, and in its place, the means for generating diffracted light or scattered light 15 may be set.

The number of light receiving elements constituting the diffracted light or scattered light detector 22 mounted to the photo detector 16 may be greater than four, and at least three light receiving elements may be enough because the laser beam 2 detects and corrects the deviation in the direction shown in FIG. 3 with arrow marks X, Y, that is, in a two-dimensional direction, and more suitably, it is desirable to concentrically arrange the light receiving elements with the optical axis center portion 0 set to the center.

In addition, in the optical axis adjustment method described above, fine-adjusting the optical axis so as to maximize the laser beam condensed by the condenser lens 6 can further improve the accuracy of the optical axis position.

It is needless to say that this optical axis adjustment method can be applied to the scattering type particle size distributing measuring equipment using not only laser 2 but also other sources of light beams.

This invention can be embodied in the configuration as described above and can take the following effects. As compared to conventional cases, the light receiving elements of the measuring portion for scattering and diffraction light detection can be arranged at a position closer to the optical axis center portion of the photo detector, enabling the measurement of particles with a larger diameter than before, and a particle distribution with a wider measuring range can be measured in one measurement cycle.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A light scattering particle size distribution measuring apparatus comprising:

a light source for providing a beam of light along an optical axis;

a sample cell for holding a specimen and receiving the beam of light for scattering and/or diffraction by particles in the specimen;

a detector assembly including a first set of detector elements for receiving the scattered and/or diffracted light from the sample cell, a second set of detector elements positioned in a common plane between the first set of detector elements and a third centroid detector element for positioning on the optical axis, the first set of detector elements extend radially outward from the optical axis and are radially spaced from each other with a radially innermost detector element positioned adjacent the third centroid detector element to enable a measurement of relatively large diameter particles, the second set of detector elements are spaced about the third centroid detector element;

a scattering and/or diffracting target member removably positioned on the optical axis, between the light source and the detector assembly, at a predetermined position to provide a predetermined diffraction pattern to the detector assembly to contact the second set of detector elements when aligned on the optical axis;

means for automatically moving the target member onto the optical axis for a calibration operation;

means for moving one of the light source and the detector assembly to align them on the optical axis;

first means for providing a measurement of the particle size distribution from output signals of the first set of detector elements when the scattering and/or diffracting target member is removed from the optical axis;

second means for measuring the predetermined scattered and/or diffraction pattern from output signals of the second set of detector elements when the scattering and/or diffracting target member is positioned on the optical axis to enable a movement of one of the light source and the detector assembly to align them on the optical axis, and means for automatically moving the target member off of the optical axis after the calibration operation.

2. The invention of claim 1 wherein the target member is an opaque member with a diffracting pin hole.

3. The invention of claim 2 wherein the detector assembly first set of detector elements include a plurality of elements forming a fan-shaped segment that has spaced gaps between elements and the second set of detector elements are positioned in a gap corresponding to the projection of the diffraction pattern from the diffracting pin hole.

4. The invention of claim 3 wherein the second set of detector elements further includes the centroid detector element positioned at the center of the fan-shaped segment.

5. The invention of claim 1 wherein the movement of one of the source of light and the detector assembly continues until equal amounts of diffracted light are measured on the second set of detector elements by the second means for measuring.

6. A light scattering particle size distribution measuring apparatus comprising:

a laser light source for providing a beam of laser light of a predetermined diameter along an option axis;

a sample cell mounted on the optical axis for holding a specimen and receiving the laser beam for scattering and/or diffraction by particles in the specimen;

a detector assembly mounted on the optical axis including a first set of detector elements for receiving the scattered and/or diffracted light from the sample cell and a second set of detector elements positioned in a common plane between the first set of detector elements, including a centroid detector positioned on the optical axis for receiving the laser beam of the predetermined diameter;

a scattering and/or diffracting target member removably positioned on the optical axis between the light source and the detector assembly, at a predetermined position to provide a predetermined diffraction pattern to the detector assembly when contacted by the laser beam;

means for moving one of the light source and the detector assembly to align them on the optical axis;

first means for providing a measurement of the particle size distribution from output signals of the first set of detector elements when the scattering and/or diffracting target member is removed from the optical axis; and second means for measuring the predetermined scattered and/or diffraction pattern from output signals of the second set of detector elements when the scattering and/or diffracting target member is positioned on the optical axis to enable a movement of one of the light source and the detector assembly to align them on the optical axis, wherein the detector assembly first set of detector elements include a plurality of elements forming a fan-shaped segment that has spaced gaps between elements and at least one of the second set of detector elements are positioned in a gap corresponding to the projection of the diffraction pattern from the target member, the first set of detector elements includes a radially innermost detector element positioned adjacent the centroid detector to enable a measurement of relatively large diameter particles.

7. The invention of claim 6 wherein the movement of one of the source of light and the detector assembly continues until equal amounts of diffracted light are measured on the second set of detector elements by the second means for measuring.

8. The invention of claim 6, wherein the target member includes a diffracting pin hole of a diameter to complement a configuration of the centroid detector.

* * * * *